(12) United States Patent
Foley et al.

(10) Patent No.: US 6,205,884 B1
(45) Date of Patent: Mar. 27, 2001

(54) HANDLE ASSEMBLY

(75) Inventors: Frank Foley, Byfleet; Brian Griffiths, Lymington; Ben Stungo, Leeds, all of (GB)

(73) Assignee: Depuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 09/247,274

(22) Filed: Feb. 10, 1999

(30) Foreign Application Priority Data

Feb. 27, 1998 (GB) .................................................. 9804281

(51) Int. Cl.$^7$ .................................................. A61B 17/00
(52) U.S. Cl. .................................................. 74/544; 606/85
(58) Field of Search ............................. 74/544, 524, 543, 74/546, 547, 548; 606/79, 85, 86, 99

(56) References Cited

U.S. PATENT DOCUMENTS

| | | | | |
|---|---|---|---|---|
| 5,089,003 | * | 2/1992 | Fallin et al. | 606/85 |
| 5,324,293 | * | 6/1994 | Rehmann | 606/85 |
| 5,443,471 | * | 8/1995 | Swajger | 606/99 |
| 5,531,750 | * | 7/1996 | Even-Esh | 606/85 X |
| 5,720,750 | * | 2/1998 | Koller et al. | 606/85 |

* cited by examiner

Primary Examiner—Mary Ann Green
(74) Attorney, Agent, or Firm—John S. Wagley

(57) ABSTRACT

A handle assembly (1) has a handle body (4), an arm (8) and a trigger mechanism (6). The handle body (4) has a recess (18) for receiving an instrument to be held by the handle assembly (1). The arm (8) pivots in relation to the handle body (4) and the trigger mechanism (6) holds the arm (8) in two positions relative to the handle body (4). A third position enables the arm (8) to be detached from the handle body (4). In the first position, the arm (8) is locked adjacent the handle body (4) such that a projection (30) from the arm (8) engages the recess (18) in which a neck of an instrument being held can be inserted.

5 Claims, 8 Drawing Sheets

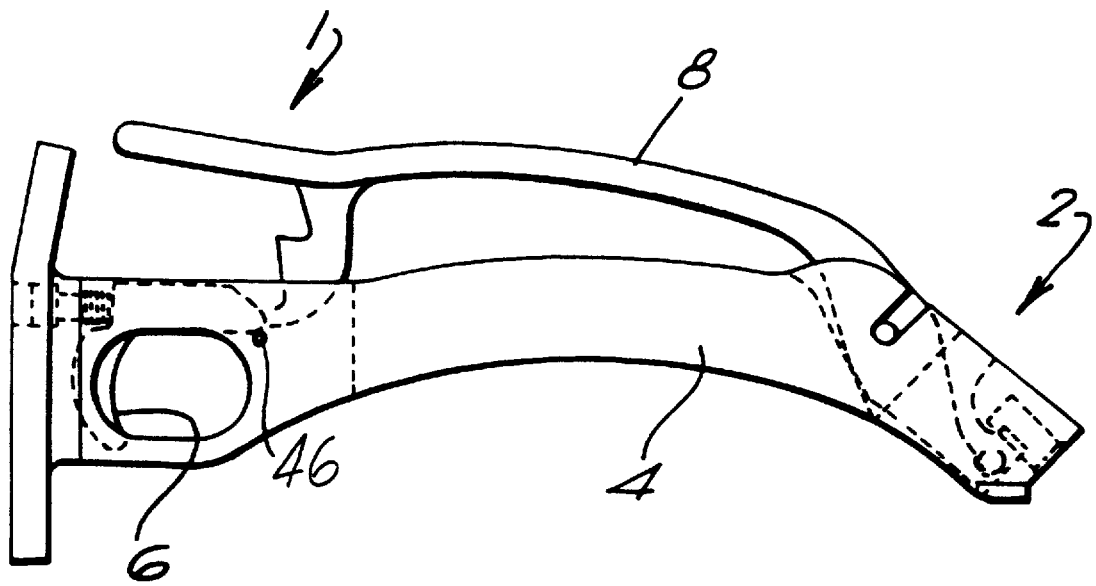
Fic. 3
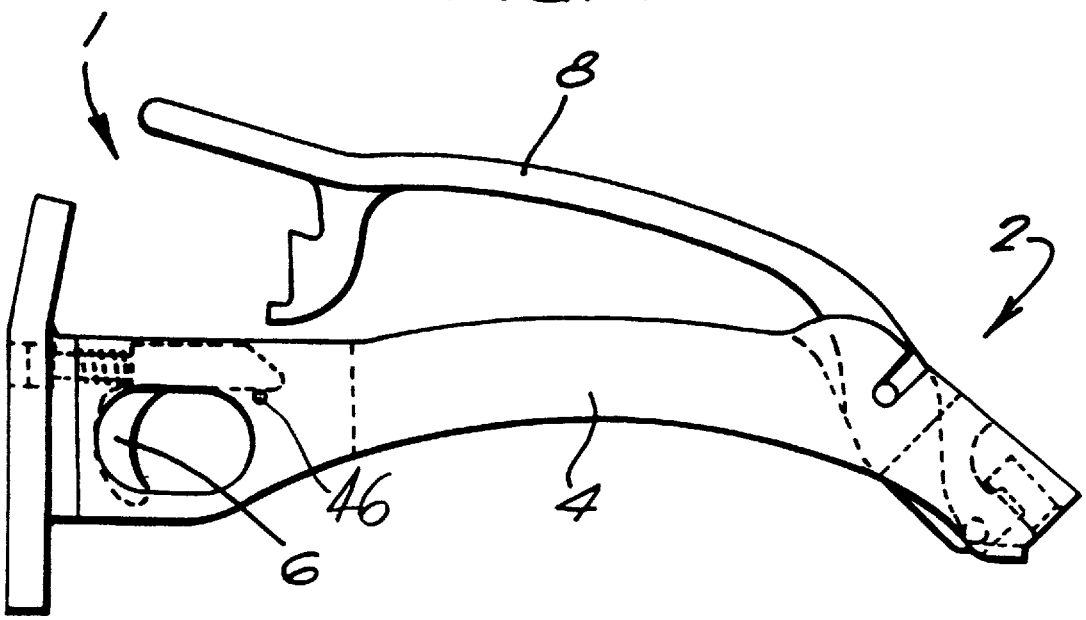
Fic. 4

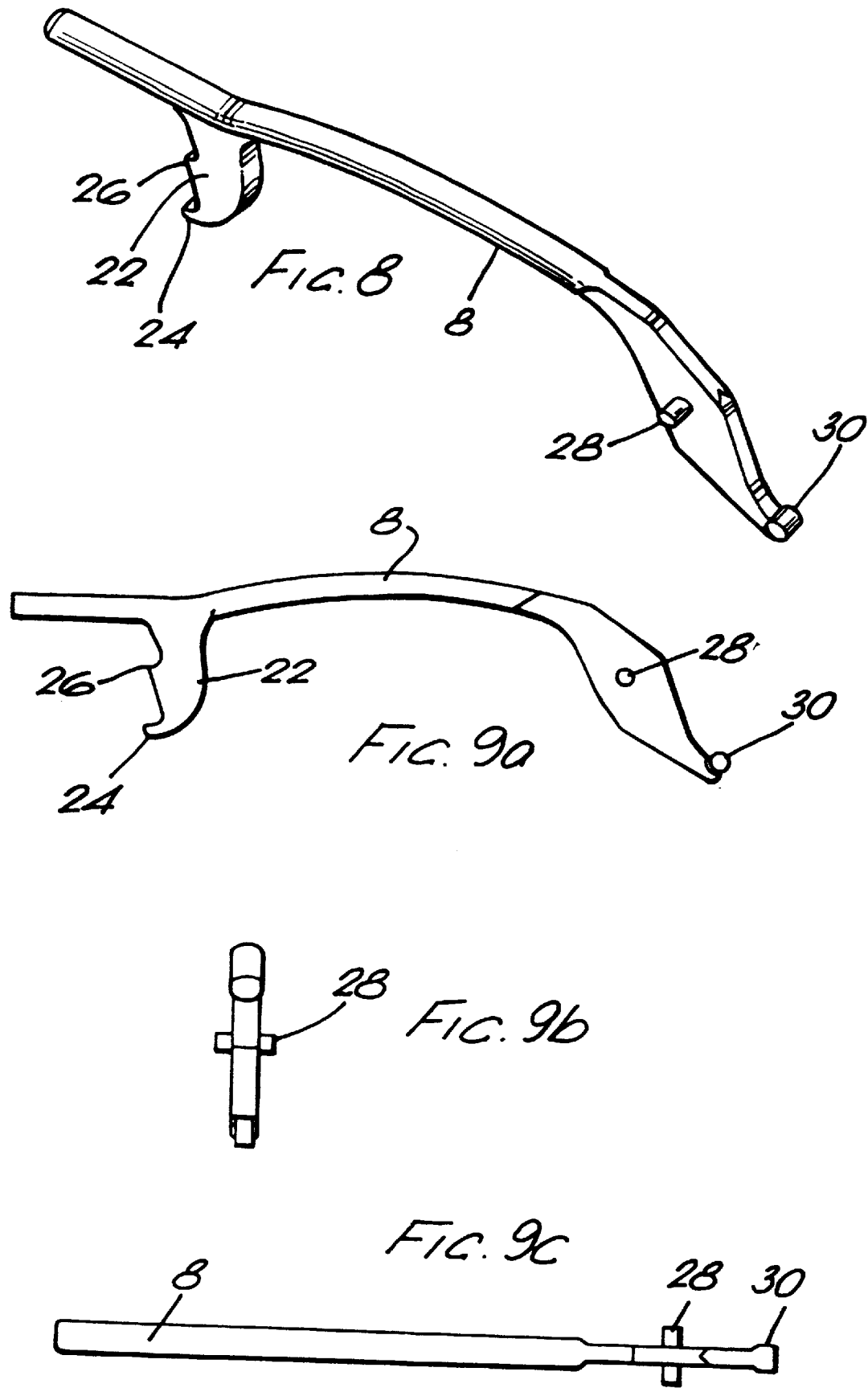

HANDLE ASSEMBLY

CROSS REFERENCE TO RELATED APPLICATIONS

Not Applicable

BACKGROUND OF THE INVENTION

This invention relates to a handle assembly for use with surgical instruments, such as broaches and tamps.

Handles are used to hold surgical instruments such as broaches to allow them to be impacted. The handle holds the instrument rigidly in order to impart control on the movement of the instrument. The use of a handle which is detachable from the instrument has the advantage that one handle can be used for a range of sizes of instruments. This is particularly useful when the instruments are broaches and a succession of instruments must be used, each instrument increasing incrementally in size.

During surgical procedures, a mixture of blood and human tissue inevitably finds its way into small places in a handle and can dry to form a glue-type mixture and become a bio-hazard. Therefore, it is essential that any handle can be easily and effectively cleaned between operations to ensure that mechanisms in the handle do not become clogged and jammed and also, more importantly, that all tissue is removed to stop cross-contamination.

BRIEF SUMMARY OF THE INVENTION

According to the present invention there is provided a handle assembly for use with surgical instruments comprising a handle body and an arm, wherein the handle body and arm have at least two relative positions, a locked position in which the arm locks an instrument in the handle body and a released position in which the arm is separable from the handle body, the handle assembly also comprising an operating mechanism for controlling the relative positions of the handle body and the arm.

Preferably, the handle body and arm have a third intermediate relative position in which the instrument is unlocked from the handle assembly whilst the arm is attached to the handle body.

Preferably, the operating mechanism is a trigger mechanism. Preferably, the trigger mechanism allows the handle body and arm to be held in their relative positions by movement of the trigger in a single direction. Most preferably, the trigger mechanism is sprung with the spring biased to in a direction to hold the handle body and the arm in their relative positions.

Preferably, the handle body and the arm are pivoted relative to one another about a pivot point. Preferably, one of the handle body and arm has a peg at the pivot point. Preferably, the other component of the handle body or arm has a slot for location over the peg. The slot is most preferably open ended to allow the separation of the handle body from the arm.

Preferably, the distal end of the arm has engaging means for engaging a portion of an instrument inserted in the handle body, in order to lock the instrument in the handle when the handle body and the arm are in their locked position.

Preferably, a trigger guide of the trigger mechanism is in a fixed relationship with the handle body and a trigger body is moveable in a single direction relative to the handle body. The arm may have at least one latch for co-operation with the trigger mechanism. Preferably, two latches are provided on the arm relating to the locked position and the unlocked position of the handle body and arm.

BRIEF DESCRIPTION OF THE DRAWINGS

Embodiments of a handle assembly in accordance with the present invention are now described by means of example only with reference to the accompanying drawings in which:

FIG. 3 is a transparent side view of the embodiment of FIG. 1 in a position rt way between the second unlocked position and a third released position;

FIG. 4 is a transparent side view of the embodiment of FIG. 1 in a third released position;

FIG. 8 is a perspective view of the arm of the handle assembly;

FIG. 9a is a side view of the arm of FIG. 8;

FIG. 9b is an end view of the arm of FIG. 8;

FIG. 9c is a top view of the arm of FIG. 8;

FIG. 10b is an end view of the trigger mechanism of FIG. 10a;

FIG. 10c is a top view of the trigger mechanism of FIG. 10a;

FIG. 12a is a transparent side view of a sub-assembly of the handle body of FIG. 6 and the trigger guide of FIG. 11a; and FIG. 12b is a top view of the sub-assembly of FIG. 12a.

DETAILED DESCRIPTION OF THE INVENTION

Figure 1:
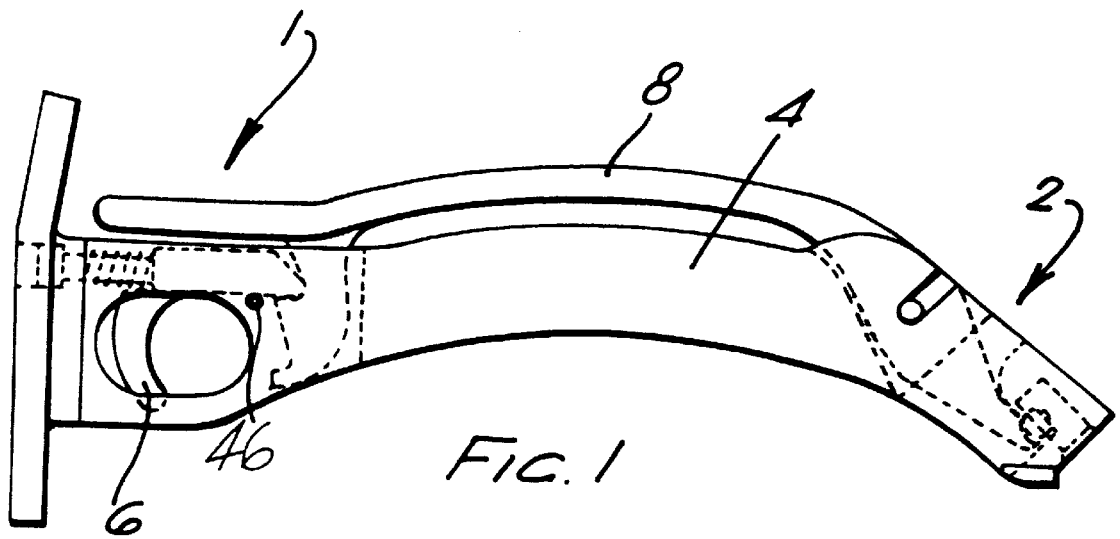
FIG. 1 is a transparent side view of a first embodiment of the handle assembly in a first locked position.
Figure 2:
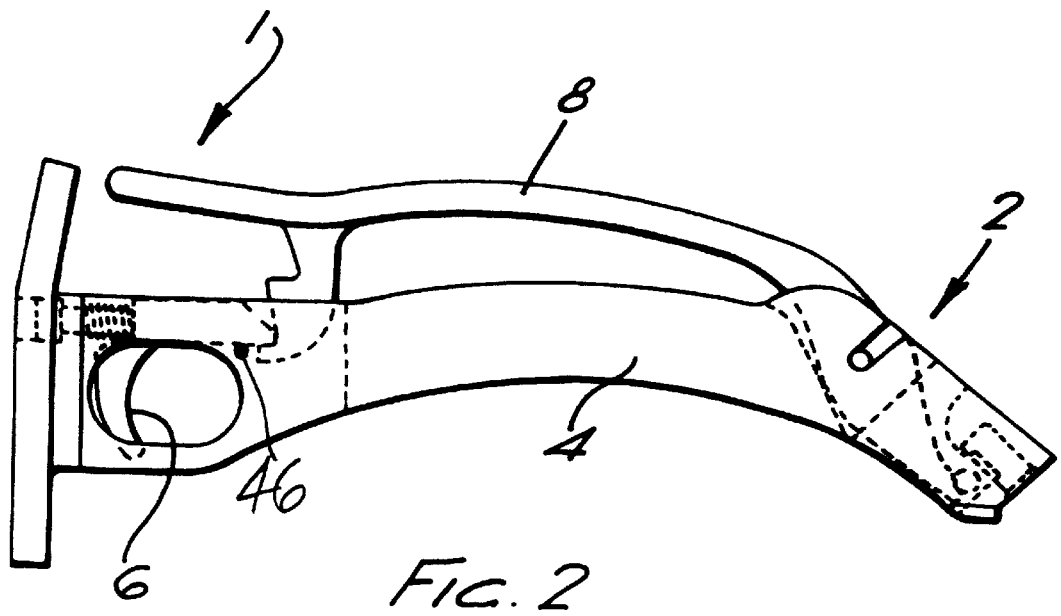
FIG. 2 is a transparent side view of the embodiment of FIG. 1 in a second unlocked position.
Figure 5:
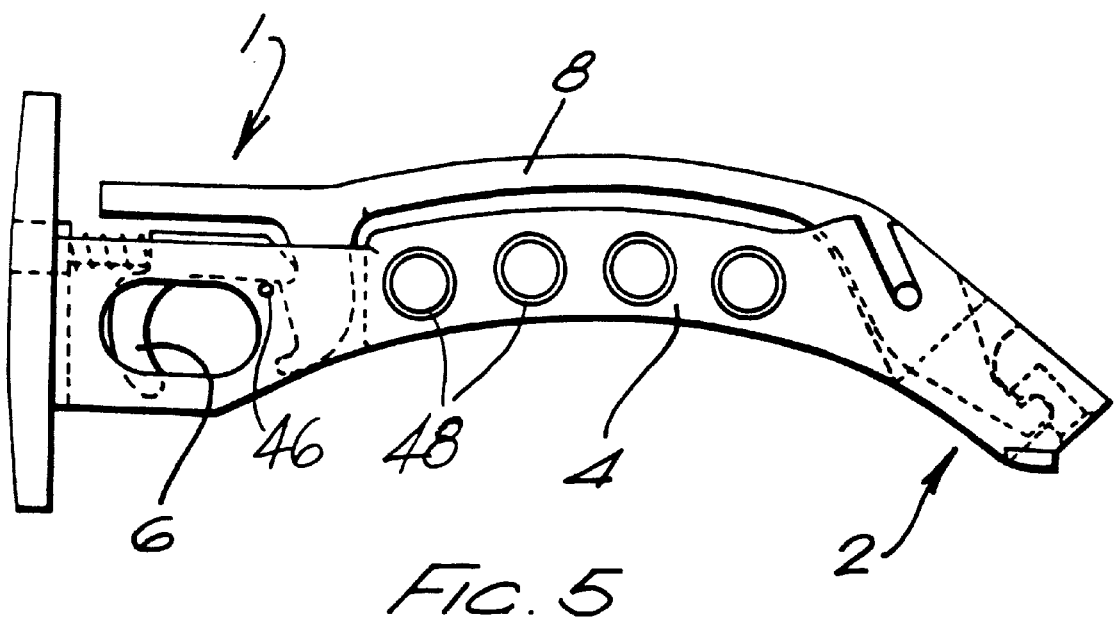
FIG. 5 is a transparent side view of a second embodiment of the handle assembly in its assembled form.
Figure 6:
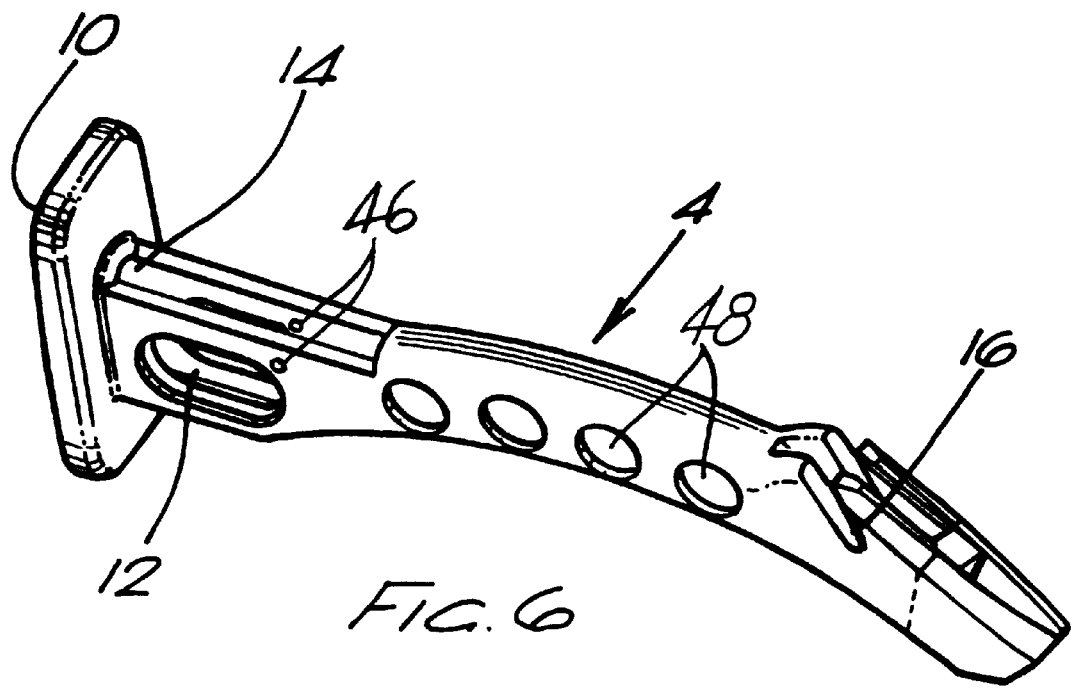
FIG. 6 is a perspective view of the handle body of the handle assembly.
Figure 7A:
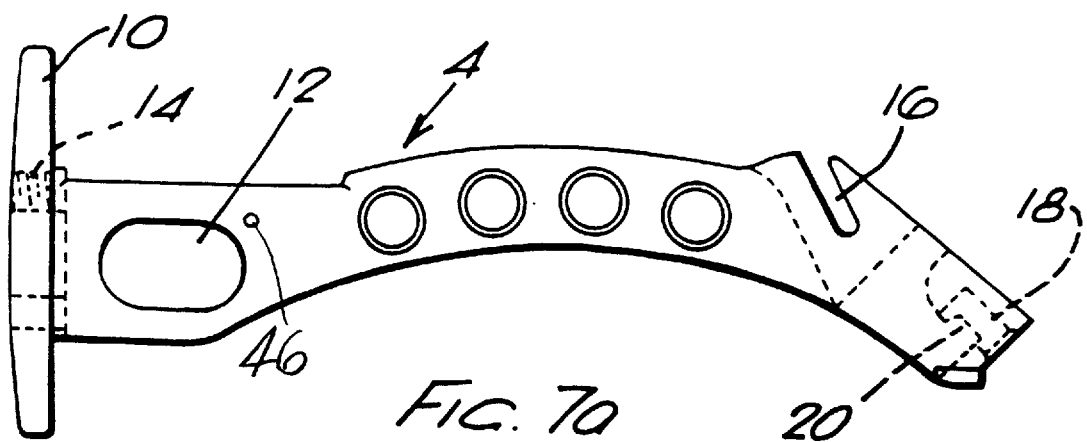
FIG. 7a is a side view of the handle body of FIG. 6.
Figure 7B:
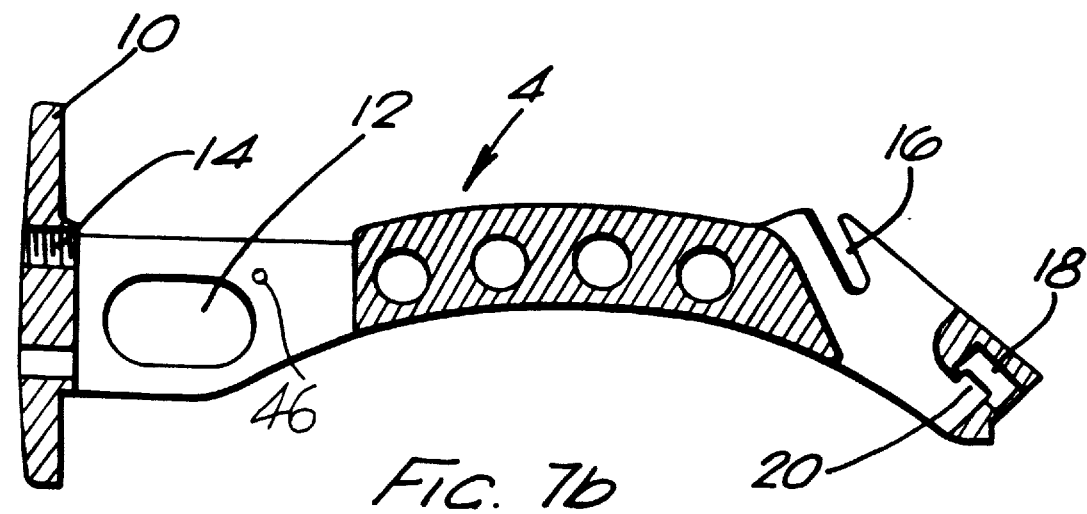
FIG. 7b is a cross-section of the handle body of FIG. 6.
Figure 7C:
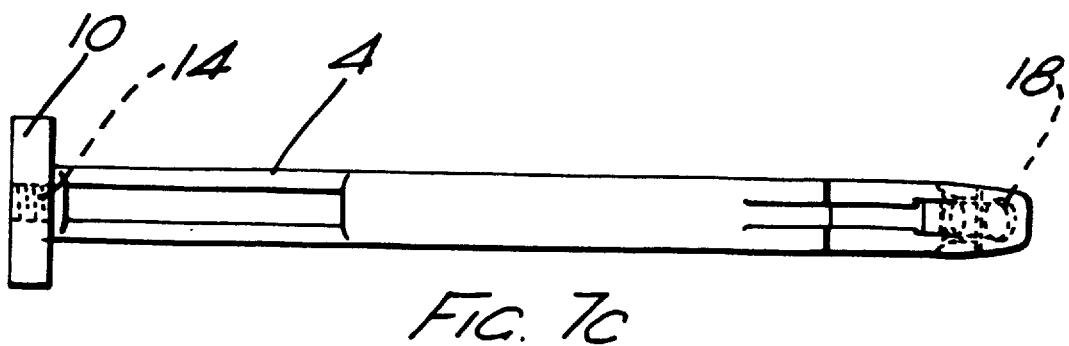
FIG. 7c is a top view of the handle body of FIG. 6.
Figure 7D:
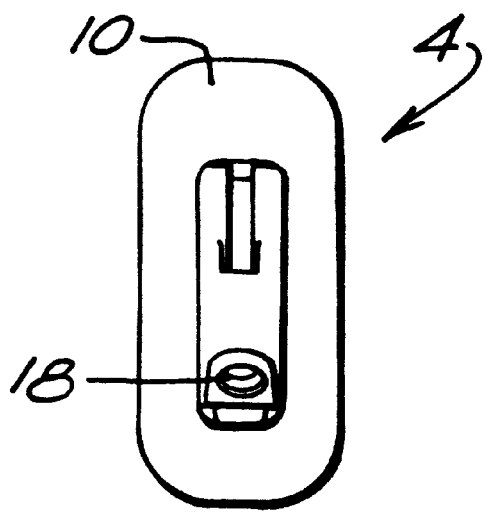
FIG. 7d is a first end view of the handle body of FIG. 6.
Figure 7E:
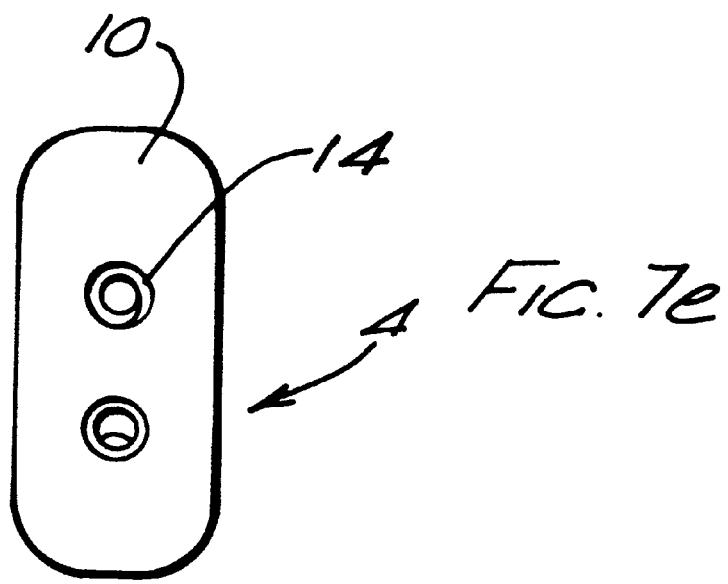
FIG. 7e is a second end view of the handle body of FIG. 6.
Figure 7F:
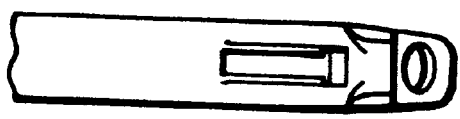
FIG. 7f is an underside view of the handle body of FIG. 6.
Figure 10A:
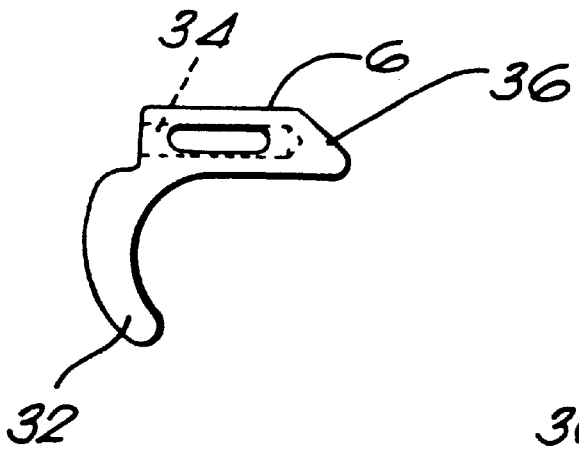
FIG. 10a is a side view of a trigger mechanism of the handle assembly.
Figure 10B:
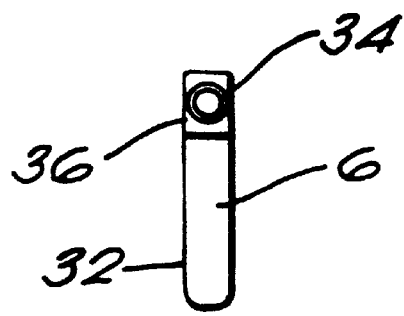
Figure 10C:
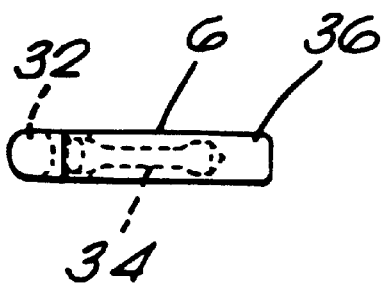
Figure 11A:
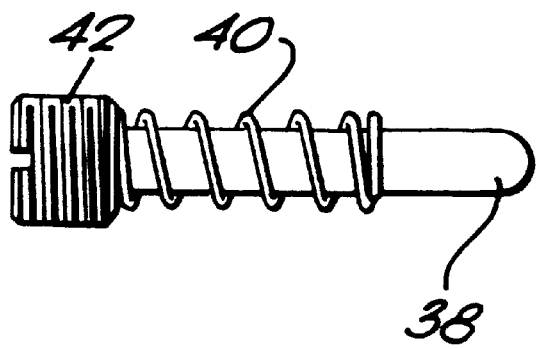
FIG. 11a is a side view of a trigger guide of the handle assembly.
Figure 11B:
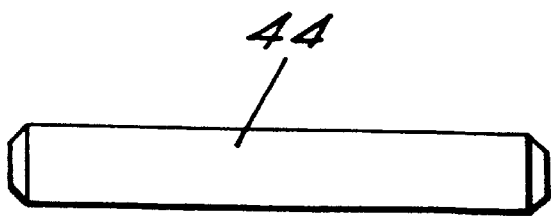
FIG. 11b is a side view of a guide pin of the handle assembly.
Figure 12A:
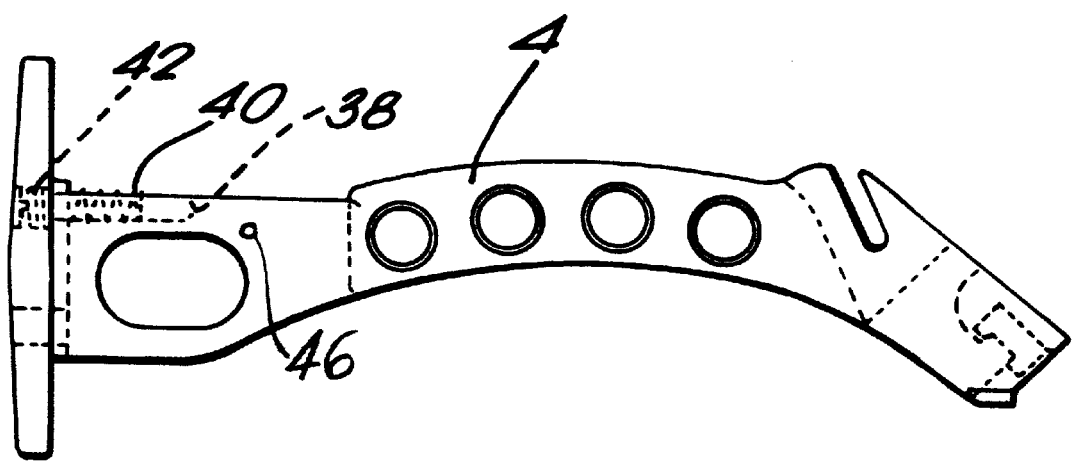
Figure 12B:
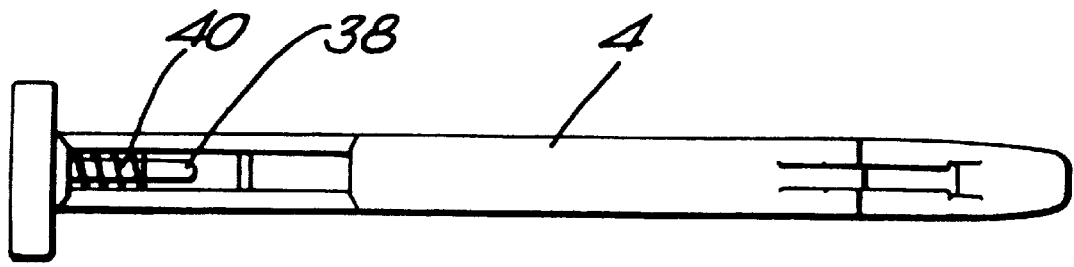

Referring to the drawings, a handle assembly 1 is provided with a locking mechanism 2 for locking a surgical instrument, such as a broach or a tamp, in the handle assembly 1. The handle assembly 1 has a handle body 4 and a locking arm 8. A trigger mechanism 6 is provided on the handle body 4 for interaction with the arm 8.

The handle body 4 is of elongate form with a first end having an end plate component 10 and an opening 12 through the handle body 4. The opening 12 provides a hole for an operator's finger for operation of the trigger mechanism 6. The plate 10 has a recess 14 which houses a trigger guide 38 in a screw threaded engagement.

The second end of the handle body 4 is provided with a cylindrical recess 18 in which a projection from the surgical instrument to be held by the handle assembly 1 can be inserted.

Part way between the two ends of the handle body 4, an open-ended slot 16 is provided which extends through the handle body 4 and engages with a peg 28 on the arm 8 which provides a pivot point about which the arm 8 and the handle 4 pivot.

The arm 8 is of an elongate form with the peg 28 at the pivot point with the handle body 4 extending on either side of the arm 8. A first end of the arm 8 has a catch mechanism 23 projecting at an approximate right angle from the arm 8 which has a first catch 24 and a second catch 26. The trigger mechanism 6 engages the catches 24, 26 and holds the arm 8 in two positions relative to the handle body 4.

A second end of the arm 8 has a projection 30 which, when the arm 8 is in a given position relative to the handle body 4, intrudes into the recess 18 in the handle body 4 in which a projection from an instrument being held is insertable.

The trigger mechanism 6 has a curved member 32 which is exposed within the opening 12 in the handle body 4 for operation by the operator's finger. The trigger mechanism 6 also has a straight member 36 orthogonal to the curved member 32 with a cylindrical recess 34 for accommodation of a trigger guide 38. The trigger guide 38 has a head 42 which is held by a screw thread attachment in the recess 14 in the plate 10 of the handle body 4. A spring 40 is provided on the trigger guide 38 between the pin head 42 and the opening of the cylindrical recess 34 in the straight member 36 of the trigger mechanism 6. The straight member 36 has a pointed end for interaction with the catch mechanism 23 of the arm 8.

The handle body 4 has a trigger guide pin 44 which extends orthogonally through the handle body 4 through holes 46 in the handle body 4. The trigger guide pin 44 holds the trigger mechanism 6 in place and guides the straight member 36.

FIGS. 1 to 4 show a first embodiment of a handle assembly 1 in which the slot 16 in the handle body 4 differs in angle to the slot 16 in the handle body 4 of a second embodiment of the handle assembly 1 shown in the remaining Figures.

The second embodiment also has a plurality of through holes 48 in the handle body 4 for the use of an alignment guide and to reduce the weight of the handle body 4.

In use, the arm 8 pivots in relation to the handle body 4 such that there are two basic positions, a first locked position, shown in FIG. 1, in which the straight member 36 of the trigger mechanism 6 engages the second catch 26 of the arm 8. In this position, the arm 8 is held by the trigger mechanism 6 close to the handle body 4 and the projection 30 at the second end of the arm 8 impinges on the recess 18 in which a neck of an instrument being held can be inserted. The projection 30 can engage with a corresponding recess in a projection from an instrument being held such that the instrument is held rigidly in relation to the handle assembly 1.

Operation of the trigger mechanism 6 by applying pressure on the curved member 32 to move the curved member 32 towards the plate 10 of the handle body 4, releases the trigger mechanism 6 from the second catch 26 and allows the arm 8 to pivot away from the handle body 4. Release of the trigger mechanism 6 causes the straight member 36 of the trigger mechanism 6 to spring into contact with the first catch 24 thereby holding the arm 8 in a second position relative to the handle body 4. In this second locked position, a surgical instrument being held by the handle assembly 1 can be extracted from the handle assembly 1 as the projection 30 has been pivoted out of the recess 18 for holding a projection from the instrument In addition to these two basic positions, there is a third released position in which the arm 8 can be removed from the handle body 4. The trigger mechanism 6 can again be operated to compress the spring 40 and release the first catch 24. The straight member 36 of the trigger mechanism 6 thereby releases the arm 8 as shown in FIG. 3. As shown in FIG. 4, the trigger mechanism 6 can then be released and the arm 8 is no longer held in attachment with the handle body 4. The arm 8 can be removed from the handle body 4 by removing the peg 28 from the slot 16 in the handle body 4.

In this way, increased access to the portion of the handle body 4 adjacent the instrument being held is achieved to facilitate cleaning of the handle assembly 1. The multiple positions of the trigger mechanism 6 allow the release of the instrument being held from the handle assembly 1 as well as release of the locking arm 8 from the handle body 4 by movement of the curved member 32 of the trigger mechanism 6 in a single direction. The curved member 32 can also be removed once the locking arm 8 has been removed, to aid cleaning.

Modifications and improvements can be made to the foregoing without departing from the scope of the present invention.

What is claimed is:

1. A handle assembly for use with surgical instruments comprising a handle body and an arm, wherein the handle body and the arm have at least two relative positions, a locked position in which the arm is adapted to lock a surgical instrument in the handle body and a released position in which the arm is separable from said handle body, said handle body having a first end and a second end, said arm having a first end and a second end, a slot near the second end of the handle body adapted to receive a peg which is located toward the second end of said arm to allow the arm to pivot around the peg, a projection on the second end of the arm adapted to fit into a, receiving recess in a surgical instrument to lock the surgical instrument to said handle assembly.

2. A handle assembly as claimed in claim 1, wherein the handle body and the arm have a third intermediate relative position in which the surgical instrument is capable of being unlocked from the handle assembly whilst the arm is attached to the handle body.

3. A handle assembly as claimed in claim 1 in which the first end of said arm includes a catch mechanism including a first catch and second catch and the first end of said handle body includes an end plate having a recess which houses a first end of a trigger guide, a second end of the trigger guide terminating in cylindrical recess of a trigger which engages the catches of said catch mechanism on said arm, and locks the arm in a position.

4. A handle assembly as claimed in claim 3, wherein the trigger mechanism allows the handle body and the arm to be held in their relative positions by movement of the trigger in a single direction.

5. A handle assembly as claimed in claim 1 wherein said slot is open ended to allow the separation of the handle body from the arm.

\* \* \* \* \*